United States Patent [19]

Syrov et al.

[11] 4,290,945
[45] Sep. 22, 1981

[54] α,α-AZO-BIS-ISOBUTYRIC ACID α,ω-BIS ALKYL ESTER DERIVATIVES AND METHOD FOR PREPARING SAME

[76] Inventors: Anatoly A. Syrov, ulitsa 3 Internatsionala, 52, kv. 51; Sergei S. Ivanchev, ulitsa Nalichnaya, 36, korpus 3, kv. 97; Oleg N. Primachenko, Suzdalsky prospekt, 38, korpus 1, kv. 13; Valentina A. Demidova, Poljustrovsky prospekt, 7, kv. 16; Boris V. Polozov, prospekt Smirnova, 20, korpus 3, kv. 32; Vladimir I. Fionov, ulitsa Komsomola, 49, kv. 5; Evgeny N. Barantsevich, ulitsa Ordzhonikidze, 59, kv. 55, all of Leningrad, U.S.S.R.

[21] Appl. No.: 91,774

[22] Filed: Nov. 6, 1979

[51] Int. Cl.$^3$ .......................... C07C 107/00
[52] U.S. Cl. .................................... 260/192
[58] Field of Search .......................... 260/192

[56] References Cited

U.S. PATENT DOCUMENTS

| | | | |
|---|---|---|---|
| 3,830,797 | 8/1974 | MacLeay et al. | 260/192 |
| 4,051,124 | 9/1977 | Moore | 260/192 |
| 4,055,714 | 10/1977 | Sheppard et al. | 260/192 X |
| 4,075,199 | 2/1978 | MacLeay et al. | 260/192 |
| 4,088,642 | 5/1978 | Sheppard et al. | 260/174 |
| 4,094,868 | 6/1978 | Chandalia et al. | 260/192 |
| 4,101,522 | 7/1978 | Sheppard et al. | 260/192 X |

FOREIGN PATENT DOCUMENTS

| | | | |
|---|---|---|---|
| 2124000 | 11/1972 | Fed. Rep. of Germany . | |
| 988253 | 4/1965 | United Kingdom | 260/192 |
| 1168406 | 10/1969 | United Kingdom | 260/192 |
| 1198782 | 7/1970 | United Kingdom | 260/192 |

Primary Examiner—Helen M. S. Sneed

[57] ABSTRACT

Novel compounds according to the present invention, i.e. derivatives of α,ω-bis-alkyl esters of isobutyric acid having the formula:

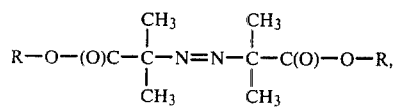

wherein R :

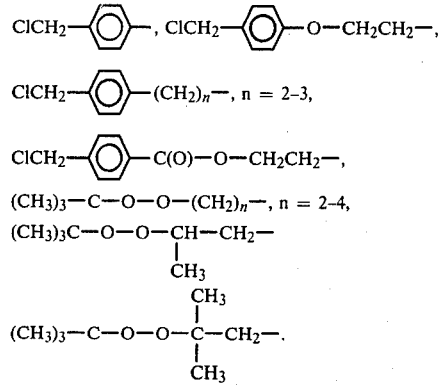

A method for preparing the above-specified novel compounds consists in reacting α,α'-azo-bis-isobutyric acid dinitrile and a saturated alkyl monohydric alcohol derivative of the formula ROH, wherein R:

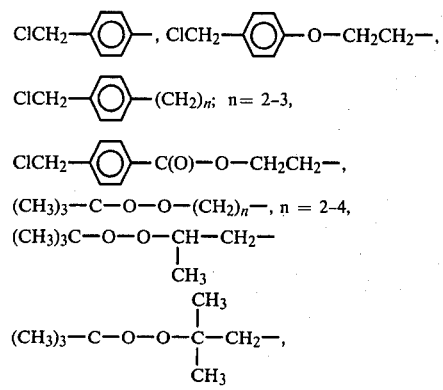

with gaseous hydrogen chloride in an organic solvent medium in the presence of 0.5–5% by mass of a water-soluble ether at a temperature within the range of from −5° to +6° C., followed by treating the resulting reaction mixture with water at a temperature of from 0° to −5° C. and isolation of the desired product.

The novel compounds according to the present invention are useful as initiators for a radical-type polymerization of ethylenically unsaturated compounds, as well as the starting products for the manufacture of reactive polymers by a simplified process.

7 Claims, No Drawings

α,α-AZO-BIS-ISOBUTYRIC ACID α,ω-BIS ALKYL ESTER DERIVATIVES AND METHOD FOR PREPARING SAME

FIELD OF THE INVENTION

The present invention relates to novel compounds, i.e. α,α'-azo-bis-isobutyric acid α,ω-bis-alkyl ester derivatives which are useful as initiators for a radical-type polymerization of reactive polymers and to a method for preparing said compounds.

BACKGROUND OF THE INVENTION

Known in the art are a whole number of radical-polymerization initiators. These may be exemplified by aliphatic azo compounds of the formula:

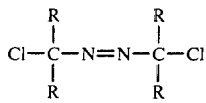

which are produced by way of chlorination of azines of the ketones with molecular chlorine in the medium of acetic acid (cf. S. Goldschmidt, B. Akchsteiner, J. Liebigs Ann.Chem., 1958, 61, 8 s. 173–185; W. Bracke, J. A. Empen, C. S. Marvel, Macromolecules, 1968, 1161, p. 465–468).

Furthermore, as radical-polymerization initiators use is made of symmetric aliphatic compounds of the formula: $X(CH_2)_nCR_1R_2N=NCR_1R_2(CH_2)_nX$,
wherein X is Cl or Br, $R_1$ and $R_2$ are each a $C_1$-$C_{20}$ alkyl, n=0 to 5 (cf. FRG Pat. No. 2,546,377 Cl. C 08 F 295/00).

These compounds when used as initiators for radical polymerization of ethylenically unsaturated monomers have a high thermal stability which hinders and frequently even precludes their application, in particular in the manufacture of reactive telechelate oligomers.

Furthermore, the above-specified compounds contain primary chloroalkyl groups possessing but a low reactivity in reactions of copolycondensation or copolyquaternization (cf. E. N. Barantzevich, N. K. Beresneva, A. E. Kalaus, T. S. Saburova "Kauchuk i Rezina", 1976, No. 9, p. 7–9; "General Practicum in Organic Chemistry", MIR Publishing House, M., 1965, p. 318; B. N. Pronin, E. N. Barantzevich, S. S. Ivanchev "Vysokomolekularnyje Soedinenija", 1977, 19(3), 455–458).

It is also known, as a radical-polymerization initiator, 2-(tert.butylazo)-2-acetoxy-4-methyl-4-(tert.butylperoxy)-pentane of the formula:

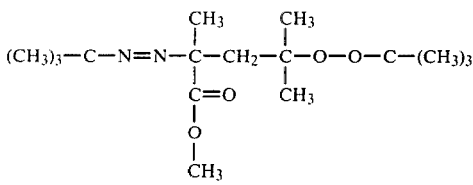

(cf. U.S. Pat. No. 4,088,642; Cl. 260/174, Int. Cl. C 07 c 107/02).

This compound, due to its asymmetry, provides, during decomposition, radicals having different chemical structure, wherefore its use as an initiator for the manufacture of telechelate oligomers with identical functional groups is impossible.

Furthermore, known as radical-polymerization initiators are α,ω-bis-alkyl esters derivatives of α,α'-azo-bisisobutyric acid of the formula:

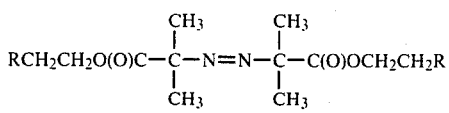

wherein R is $CH_2CH_2Cl$, $-(CH_2CH_2O)_nOH$.

These compounds are prepared by treating α,α'-azo-bis-isobutyric acid dinitrile and ethylene chlorohydrin or ethylene glycol or polyethylene glycol with hydrogen chloride in an organic solvent medium, followed by treating the resulting reaction mixture with water and isolation of the desired product by distilling-off the solvent from the desired product, extraction or recrystallization of the desired product. (Cf. FRG Offenlegungschrift No. 2,124,000 Cl. C07 C 107/02).

These compounds contain, as reactive functional groups, only $OCH_2CH_2Cl$ or $-OCH_2CH_2OH$, whereby the field of their application in chemical reactions is limited, especially in such reactions as radical polymerization, polyquaternization, polycondensation.

The novel compounds according to the present invention, i.e. α,ω-bis-alkyl-ester derivatives of α,α'-azo-bis-isobutyric acid are hitherto unknown from the literature.

BRIEF SUMMARY OF THE INVENTION

It is an object of the present invention to provide such novel compounds—derivatives of α,α'-azo-bis-isobutyric acid, α,ω-bis-alkyl esters which would make it possible, in the case of using them as starting products in reactions of polycondensation or polyquaternization, or as initiators of radical-type polymerization of ethylenically-unsaturated compounds, to produce, through a simple process, novel high-molecular compounds possessing improved properties, for example high-molecular compounds with high impact strength, heat- and frost-resistance, gas-impermeability and high dielectric characteristics.

This object is accomplished by that novel compounds—alkyl esters of the formula:

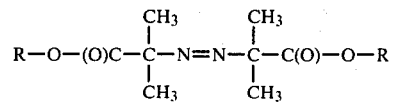

wherein R:

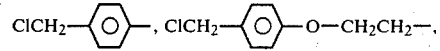

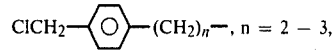

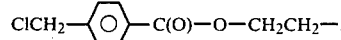

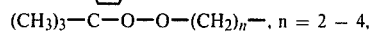

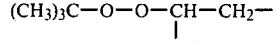

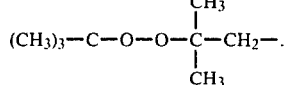

are prepared by reacting α,α''-azo-bis-isobutyric acid dinitrile and an alkyl saturated monohydric alcohol derivative of the formula ROH, wherein R is ClCH$_2$—⟨O⟩—, ClCH$_2$—⟨O⟩—O—CH$_2$CH$_2$—, ClCH$_2$—⟨O⟩—(CH$_2$)$_n$—, n = 2 – 3;

ClCH$_2$—⟨O⟩—C(O)—O—CH$_2$CH$_2$—, (CH$_3$)$_3$—C—O—O—(CH$_2$)$_n$—, n = 2 – 4;

(CH$_3$)$_3$C—O—O—CH—CH$_2$—
            |
            CH$_3$

CH$_3$
                    |
(CH$_3$)$_3$—C—O—O—C—CH$_2$—,
                    |
                    CH$_3$ with gaseous hydrogen chloride in an organic solvent medium in the presence of 0.5 to 5% by mass of a water-soluble ether at a temperature within the range of from −5° to +6° C., followed by treating the resulting reaction mixture with water at a temperature of from 0° to −5° C. and isolating the desired product.

It is desirable to use, as the organic solvent, benzene, pentane, diethyl ether, methylene chloride.

In order to increase the desired product yield, it is advisable that the process of interaction of said starting components be conducted in the presence of tetrahydrofuran, dioxane, trioxane, diethylene or triethylene glycol dimethylate.

The resulting derivatives of α,α'-azo-bis-isobutyric acid α,ω-bis-alkyl esters are useful as initiators for a radical-polymerization of ethylenically unsaturated compounds, as well as the starting products for the production of novel, hitherto unknown reactive polymers possessing improved properties such as impact strength, heat- and frost-resistance, improved dielectric characteristics and oligomers with reactive functional groups.

Moreover, the method for producing derivatives of α,α'-azo-bis-isobutyric acid, α,ω-bis-alkyl esters according to the present invention is a single-stage and simple process, since inexpensive and readily available products are employed as the starting materials.

DETAILED DESCRIPTION OF THE INVENTION

The novel compounds according to the present invention, i.e. derivatives of α,α'-azo-bis-isobutyric acid α,ω-bis-alkyl esters have the following generic formula:

CH$_3$      CH$_3$
                |          |
R—O—(O)C—C—N=N—C—C(O)—O—R,
                |          |
                CH$_3$      CH$_3$ wherein R:

ClCH$_2$—⟨O⟩—, ClCH$_2$—⟨O⟩—O—CH$_2$CH$_2$—,

ClCH$_2$—⟨O⟩—(CH$_2$)$_n$—, n = 2 – 3;

ClCH$_2$—⟨O⟩—C(O)—O—CH$_2$CH$_2$—, (CH$_3$)$_3$—C—O—O—(CH$_2$)$_n$—, n = 2 – 4;

-continued (CH$_3$)$_3$C—O—O—CH—CH$_2$—;
            |
            CH$_3$

CH$_3$
                    |
(CH$_3$)$_3$—C—O—O—C—CH$_2$—
                    |
                    CH$_3$

These compounds comprise either a light-yellow liquid or white crystalline prism-like solid substances with a specific odour. The temperatures at which the half-decomposition period of azo and peroxy groups of the compounds of the present invention is 10 hours are equal to 70° and 130° C. respectively.

The structure of the compounds produced according to the present invention is identified by various methods of physicochemical analysis.

IR-spectra are taken in a thin layer of CCl$_4$ using a UR-10 instrument available from "Karl-Zeiss", GDR, within the range of from 800 to 1,800 cm$^{-1}$.

UV-spectra are recorded in ethylbenzene using a CF-8 instrument available from "LOMO" production enterprise, Leningrad, USSR, at 365 nm.

PMR-spectrum is recorded using a "Perkin Elmer" (USA) instrument at 80 MHz relative to the internal standard-hexamethyldisiloxane. Molecular mass is determined either cryoscopically in dioxane or benzene, or by measuring thermal effects of condensation (MTEC method).

Thin-layer chromatography of the resulting compounds is effected using ready "Silufol" plates with a layer of silica gel applied onto an aluminium substrate produced by "Kavalier" company, Czechoslovakia. As the eluent use is made of a mixture of toluene, hexane, methanol and acetic acid in the volumetric ratio of 12:5:2:1 respectively.

Peroxide compounds are developed by spraying plates taken after application of a solution of the test compounds and elution with a 2% aqueous solution of HJ, followed by heating the plate to the temperature of 70° C. for 5 minutes.

The process for producing derivatives of α,α'-azo-bis-isobutyric acid α,ω-bis-alkyl esters resides in that α,α'-azo-bis-isobutyric acid dinitrile and an alkyl saturated monohydric alcohol derivative of the formula ROH,
wherein
R is ClCH$_2$—⟨O⟩—, ClCH$_2$—⟨O⟩—O—CH$_2$CH$_2$—, ClCH$_2$—⟨O⟩—(CH$_2$)$_n$—, n = 2 – 3;

ClCH$_2$—⟨O⟩—C(O)—OCH$_2$CH$_2$—, (CH$_3$)$_3$—C—O—O—(CH$_2$)$_n$—, n = 2 – 4, (CH$_3$)$_3$C—O—O—CH—CH$_2$—,
            |
            CH$_3$

CH$_3$
                    |
(CH$_3$)$_3$—C—O—O—C—CH$_2$—
                    |
                    CH$_3$ is reacted with gaseous hydrogen chloride in an organic solvent medium in the presence of 0.5 to 5% by mass of a water-soluble ether, followed by treatment of the resulting reaction mixture with water.

For the purpose of a higher yield of the desired product, as the organic solvent use is made of benzene, pentane, diethyl ether and methylene chloride, while as the water-soluble ether use is made of tetrahydrofuran, dioxane, trioxane, diethylene glycol or triethylene glycol dimethylate.

The above-specified amount of the water-soluble ether of 0.5–5% by mass is optimal. The addition of the catalyst in an amount of below 0.5% by mass is inefficient, while above 5% by mass—undesirable due to associated difficulties of separation and further use of the catalyst. As a result of the reaction, nitrile group of $\alpha,\alpha'$-azo-bis-isobutyric acid dinitrile is converted to an estereal group.

In general, the synthesis of derivatives of $\alpha,\alpha'$-azo-bis-isobutyric acid $\alpha,\omega$-bis-alkyl esters is effected according to the following scheme:

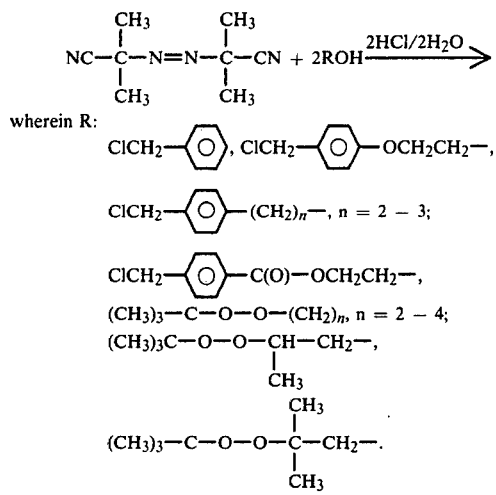

The interaction of gaseous hydrogen chloride with the starting components is carried out at a temperature within the range of from $-5°$ to $+6°$ C. The subsequent treatment of the resulting reaction mixture with water is effected at a temperature of from $0°$ to $-5°$ C.

In order to increase the desired product yield, the starting components are employed in the following weight proportion relative to the organic solvent, or gaseous hydrogen chloride, or water: 1:3 to 20 respectively.

On composition of the process the resulting reaction mass is treated with water at a temperature within the range of from $0°$ to $-5°$ C. Without this water treatment of the reaction mass it is impossible to ensure formation and isolation of the desired products.

Recovery of the derivatives of $\alpha,\alpha'$-azo-bis-isobutyric acid, $\alpha,\omega$-bis-alkyl esters can be performed by any conventional technique. Thus, recovery of the resulting products from the cooled reaction mass is effected by separation of the aqueous phase containing water-soluble ethers and hydrogen chloride from the solvent containing the desired product, residual amounts of the unreacted components and hydrogen chloride. Then the solvent is washed with a 5% solution of sodium bicarbonate and water to obtain the negative reaction on chloride ions. Thereafter, the solvent is dried with anhydrous sodium sulphate and distilled-off in vacuum to give the desired product.

To ensure an additional purification of the desired product from contaminants, it is either recrystallized from a mixture consisting of petroleum ether, diethyl ether, or passed through a chromatographic column using alumina as a sorbent.

For a better understanding of the present invention, some specific Examples are given hereinbelow by way of illustration.

EXAMPLE 1

Into a reaction vessel with a bubbling unit there are charged 5 g (0.0305 mol) of $\alpha,\alpha'$-azo-bis-isobutyric acid dinitrile, 20 g (0.149 mol) of $\beta$-hydroxyethyltert. butylperoxide, 0.5 ml (1.8% by mass of the total mass of the reagents) of tetrahydrofuran distilled with calcium hydride and dry hydrogen chloride is passed through the resulting suspension at the temperature of $0°$ C. at the rate of 1 l/hr for 5 hours till a complete dissolution of $\alpha,\alpha'$-azo-bis-isobutyric acid dinitrile. Then the resulting reaction mixture is kept in a refrigerator at the temperature of $+6°$ C. for 20 hours. Thereafter, it is treated with 100 ml of ice-cold water for two hours at the temperature of $0°$ C. under vigorous stirring. After stratification of the resulting reaction mass into two layers, the oily phase containing the desired product, residual amounts of the starting agents and hydrogen chloride is separated from water and washed with 150–200 ml of a 5% solution of sodium bicarbonate and water till no chlorine ions are detected and then dried over anhydrous sodium sulphate. The solution containing the desired product is passed through a column with alumina to remove impurities. The solvent is distilled-off from the desired product in vacuum of 0.01 mm Hg.

There are obtained 8 g (61% of the theory) of a light-yellow product which corresponds, after identification, to $\alpha,\omega$-bis(tert.-butylperoxyethyl) ester of $\alpha,\alpha'$-azo-bis-isobutyric acid.

The data of physico-chemical analysis are as follows:
Elemental analysis: Found, % by mass: C 56.1; H 9.0; N 6.6. $C_{20}H_{33}O_8N_2$. Calculated, % by mass: C 55.30; H 8.76; N 6.45.

Gas number: Found 52 cm$^3$/g; calculated 52 cm$^3$/g.

In the IR-spectrum (CCl$_4$, thin-layer) an absorption band with the frequency $\nu=1,740$ cm$^{-1}$ is observed which corresponds to C=O bond.

In the UV-spectrum (ethylbenzene) maximum of the absorption band is observed with the wavelength $\lambda_{max}=365$ nm and coefficient $\epsilon=26$ which corresponds to N=N bond.

In PMR-spectrum observed are lines with chemical shifts $\delta=1.16$ ppm, 1.38 ppm; 4.00 ppm; 4.22 ppm relative to hexamethyldisiloxane corresponding to the groups: O—C(CH$_3$)$_3$; N—C—CH$_3$; O—CH$_2$—CH$_2$—O respectively.

A thin-layer chromatogram of the resulting desired product is obtained on a "Silufol" plate produced by "Kavalier", a Czechoslovakian company. As the eluent use is made of a mixture consisting of toluene, hexane, methanol, acetic acid taken in the following volumetric ratio: 12:5:2:1 respectively. A developer (2% aqueous solution of HJ) after heating the plate to the temperature of $70°$ C. for 5 minutes shows one blue spot with the resolution factor of $R_f=0.60$.

| | |
|---|---|
| Refractive index $n_D^{20}$ | 1.4410 |
| Density $d_4^{20}$ | 1.014 g/cm$^3$. |

EXAMPLE 2

Into a reaction vessel provided with a bubbling unit and a stirrer there are charged 5 g (0.0305 mol) of $\alpha,\alpha'$-azo-bis-isobutyric acid dinitrile, 8.17 g (0.0610 mol) of $\beta$-hydroxyethyltert.butylperoxide, 0.15 ml (0.5% by mass) of tetrahydrofuran distilled over calcium hydride and 20 ml of benzene distilled over sodium. Dry gaseous hydrogen chloride is passed through the resulting suspension at the rate of 1 l/hr for 4 hours at the temperature of +6° C. till a complete dissolution of $\alpha,\alpha'$-azo-bis-isobutyric acid dinitrile. Then the resulting reaction mixture is kept in a refrigerator for 18 hours at the temperature of +6° C. Afterwards, the reaction mixture is treated, under vigorous stirring at the temperature of −5° C. with 100 ml of ice-cold water for 2 hours. A further separation of the product is conducted in a manner similar to that described in the foregoing Example 1. There are obtained 7.95 g (60.1% of the theory) of $\alpha,\omega$-bis(tert.butylperoxyethyl) ester of $\alpha,\alpha'$-azo-bis-isobutyric acid having the same physicochemical characteristics as in Example 1 hereinabove. The resulting compound is useful as an initiator of polymerization of butadiene and obtained in the following manner.

Into a 150 ml glass ampule there are charged 2.6 g (6.0×10$^{-3}$ mol) of $\alpha,\omega$-bis(tert.butylperoxyethyl)ester of $\alpha,\alpha'$-azo-bis-isobutyric acid, 40 ml of acetone and 30 ml of butadiene and the mixture is kept under stirring for 20 hours at the temperature of 70° C. On completion of polymerization the unreacted monomer is outgassed and the formed oligobutadiene is washed for 4 times with an aqueo-acetone mixture (1:1 by volume) to remove completely the residual amounts of the initiator and its decomposition products. Raw oligobutadiene is dried at a temperature within the range of from 60° to 80° C. under a residual pressure of 2 to 5 mm Hg to give 5.8 g of oligobutadiene; the yield is equal to 30% of the theoretical value; molecular mass is 2,600.

EXAMPLE 3

The process is conducted as in the foregoing Example 2, with the only exception that as the solvent use is made of 25 ml of diethyl ether and as the catalyst use is made of 1.5 ml (5% by mass) of dioxane. The reaction temperature is −5° C. There are obtained 10.45 g (79.0% of the theoretical value) of $\alpha,\omega$-bis(tert.butylperoxyethyl) ester of $\alpha,\alpha'$-azo-bisisobutyric acid having the same physico-chemical characteristics as in Example 1.

EXAMPLE 4

The process is conducted just as in Example 2 hereinbefore with the only exception that as the solvent use is made of 20 ml of methylene chloride and as the catalyst—1.2 ml (3% by mass) of dioxane. The reaction temperature is 0° C. There are obtained 8.60 g (65.1% of the theoretical value) of $\alpha,\omega$-bis(tert.butylperoxyethyl)ester of $\alpha,\alpha'$-azo-bis-isobutyric acid having the same physico-chemical characteristics as in Example 1 hereinbefore.

EXAMPLE 5

The process is conducted as in Example 2, but the only difference is in that as the catalyst use is made of 0.2 ml (0.6% by mass) of dimethyl ether of ethylene glycol. There are obtained 10.1 g (76% of the theoretical value) of $\alpha,\omega$-bis(tert.butylperoxyethyl) ester of $\alpha,\alpha'$-azo-bis-isobutyric acid having the same physico-chemical characteristics as in the foregoing Example 1.

EXAMPLE 6

The process is conducted as in Example 2, except that use is made of 15 g (0.112 mol) of $\beta$-hydroxyethyltert-.butyl peroxide. There are obtained 8.03 g (60.7% of the theoretical value) of $\alpha,\omega$-bis(tert.butylperoxyethyl)ester of $\alpha,\alpha'$-azo-bis-isobutyric acid having the same physico-chemical characteristics as in Example 1 hereinbefore.

EXAMPLE 7

The process is carried out as in Example 2, except that as the solvent use is made of 20 ml diethyl ether and as the catalyst—0.3 ml (1% by mass) of trioxane. The reaction temperature is 0° C. There are obtained 9.4 g (71% of the theoretical value) of $\alpha,\omega$-bis(tert.butylperoxyethyl) ester of $\alpha,\alpha'$-azo-bis-isobutyric acid having the same physico-chemical parameters as in Example 1. The resulting compound is useful as a starting product for the manufacture of reactive polymers which is obtained by the method described hereinbelow.

Into an ampule there is charged 1.05 g (2.4×10$^{-3}$ mol) of $\alpha,\omega$-bis(tert.butylperoxyethyl) ester of $\alpha,\alpha'$-azo-bis-isobutyric acid, 10 g of methylmethacrylate and 0.01 g of tetramethylene pentamine. Oxygen dissolved in the monomer is removed by evacuation.

The ampule is thermostatted at the temperature of 25° C. After 24 hours the degree of conversion of methylmethacrylate to polymer is 90%. The presence of azo group in the main chain is proven by the ability of the resulting product of initiating radical polymerization of styrene with the formation of block-copolymers of the ABA type. To this end, the thus-obtained product is dissolved in styrene (20 g) and heated at the temperature of 60° C. for the period of 24 hours. The formed polymer is dissolved in benzene and reprecipitated in ethanol. The presence of the block-copolymer is identified from the fact that a 14% solution of the final product in chloroform is not stratified for the period of 13 days, while a mixture of 14% solutions of polystyrene and polymethylmethacrylate taken in the ratio of 1:1 in chloroform and produced under similar conditions gets stratified within 15 minutes.

EXAMPLE 8

The process is conducted as in Example 2 hereinbefore, with the exception that as the solvent use is made of 20 ml of methylene chloride and as the catalyst—0.15 ml (0.5% by mass of diethylene glycol dimethylate. The reaction temperature is −5° C. There are obtained 9.05 g (68.3% of the theoretical value) of $\alpha,\omega$-bis-(tert.butylperoxyethyl) ester of $\alpha,\alpha'$-azo-bis-isobutyric acid having the same physico-chemical constants as in the foregoing Example 1.

EXAMPLE 9

The process is conducted as in Example 2, with the only difference that as the catalyst use is made of 1.1 g (3% by mass) of triethylene glycol dimethylate. There are obtained 8.9 g (67% of the theoretical value) of $\alpha,\omega$-bis(tert.butylperoxyethyl) ester of $\alpha,\alpha'$-azo-bis-isobutyric acid having the same physico-chemical characteristics as in Example 1.

The resulting compound is useful as an initiator of a radical polymerization of styrene effected by the procedure described hereinbelow.

100 ml of styrene containing $5.10^{-4}$ mol of α,ω-bis(-tert.butylperoxyethyl) ester of α,α'-azo-bis-isobutyric acid are heated to the temperature of 70° C. and maintained at this temperature until the desired product is formed.

The polymerization rate is controlled by increasing density of the reaction mass demonstrating the formation of polystyrene.

At the conversion of 5% the rate of polymerization is $1.1 \times 10^{-4}$ mol/l, at the conversion of 10%—$1.0 \times 10^{-4}$ mol/l.

For the purpose of comparison, the rate of polymerization in the absence of the initiator at conversion values of 5 and 10% is $4.5 \times 10^{-6}$ mol/l.

EXAMPLE 10

The process is conducted as in Example 2, except that as the hydroxyalkyltert.butylperoxide use is made of Γ-hydroxypropyltert.butyl peroxide. There are obtained 12.6 g (90% by mass of the theoretical value) of α,ω-bis(tert.butylperoxypropyl) ester of α,α'-azo-bis-isobutyric acid. This compound comprises a yellowish liquid. The physico-chemical characteristics of the compound are as follows.

Elemental composition: Found, % by mass: C 57.10 H 9.01 N 6.08. $C_{22}H_{42}O_8N_2$. Calculated, % by mass: C 57.14 H 9.09 N 6.06.

In the IR-spectrum (CCl$_4$, thin layer) there is observed an absorption band with the frequency $\nu=1,470$ cm$^{-1}$ corresponding to the bond C=O. In the UV-spectrum (ethylbenzene) there is observed maximum of the absorption band at the wavelength $\lambda_{max}=465$ nm corresponding to the bond N=N and coefficient $\epsilon=26$.

Cryoscopic molecular mass (benzene): Found: 467. Calculated: 462.

EXAMPLE 11

The process is conducted as in Example 2, except that as the hydroxyalkyltert.butylperoxide use is made of σ-hydroxybutyltert.butylperoxide.

There are obtained 14.2 g (95% of the theoretical value) of α,ω-bis(tert.butylperoxybutyl) ester of α,α'-azo-bis-isobutyric acid. The product comprises a light-yellow liquid. The compound has the following physico-chemical characteristics:

elemental analysis Found, % by mass: C 58.81 H 9.30 N 5.80. $C_{24}H_{46}O_8N_2$. Calculated, % by mass: C 58.78 H 9.39 N 5.71.

In the IR-spectrum (CCl$_4$, thin layer) there is observed an absorption band with the frequency of 1,740 cm$^{-1}$ corresponding to the bond C=O.

In the UV-spectrum (ethylbenzene) there is observed the absorption band maximum at the wavelength $\lambda_{max}=365$ nm corresponding to the bond N=N and coefficient $\epsilon=26$.

Cryoscopic molecular mass (in dioxane): Found: 495. Calculated: 490.

The resulting compound is useful as an initiator of the radical polymerization of butadiene which is obtained following the procedure of Example 2, except that instead of α,ω-bis(tert.butylperoxybutyl) ester of α,α'-azo-bis-isobutyric acid as the initiator of polymerization use is made of 2.94 g ($6.0 \times 10^{-3}$ mol) of α,ω-bis(tert.butylperoxybutyl) ester of α,α'-azo-bis-isobutyric acid. There are obtained 5.9 g of oligobutadiene. The yield is equal to 30% of the theoretical value.

EXAMPLE 12

The process is conducted in a manner similar to that described in Example 2 hereinbefore, except that as the hydroxyalkyltert. butylperoxide use is made of β-hydroxyisopropyltert. butylperoxide taken in the amount of 15 g (0.101 mol).

There are obtained 12.1 g (87% of the theoretical value) of α,ω-bis(tert.butylperoxy-α-/methyl/ethyl)ester of α,α'-azo-bis-isobutyric acid. This compound comprises a light-yellow liquid. The product has the following characteristics:

Elemental analysis: Found, % by mass: C 57.20 H 9.09 N 6.05 $C_{22}H_{42}O_8N_2$. Calculated, % by mass: C 57.14 H 9.09 N 6.06.

IR- and UV-spectra contain characteristic absorption bands corresponding to the functional groups identic to those described in Example 1.

Cryoscopic molecular mass (in dioxane): Found: 469. Calculated: 462.

EXAMPLE 13

The process is conducted in the same manner as in Example 2, except that as the hydroxyalkyltert.butylperoxide use is made of β-hydroxy-α,α'-bis-(methyl)-ethyltert.butyl peroxide. There are obtained 13.3 g (89% of the theoretical value) of α,ω-bis(tert.butylperoxy-α,α'-bis/methyl/ethyl) ester of α,α'-azo-bis-isobutyric acid. This compound comprises a light-yellow liquid. The product has the following physico-chemical characteristics.

Elemental analysis: Found, % by mass: C 58.80 H 9.33 N 5.69. $C_{24}H_{46}O_8N_2$. Calculated, %: by mass: C 58.78 H 9.39 N 5.71.

Intrinsic absorption bands characteristic for the functional groups of the obtained compound are identic to those found for the compound of Example 1 hereinbefore.

Cryoscopic molecular mass (in benzene).
Found 493. Calculated 490.

The thus-produced compound is useful as an initiator for a radical polymerization of butadiene which is obtained as in Example 2, except that instead of α,ω-bis(-tert.butylperoxyethyl) ester of α,α'-azo-bis-isobutyric acid as the initiator for polymerization of butadiene use is made of 2.94 g ($6.0 \times 10^{-3}$ mol) of α,ω-bis(tert.butylperoxy-α,α'-bis/methyl/ethyl) ester of α,α'-azo-bis-isobutyric acid. There are obtained 5.8 g of oligobutadiene. The yield is equal to 30% of the theoretical value.

EXAMPLE 14

Into a reaction vessel with a bubbling unit there are charged 5 g (0.0305 mol) of α,α'-azo-bis-isobutyric acid dinitrile, 11.37 g (0.061 mol), mono-n-(chloromethyl)-phenylate of ethylene glycol, 0.5 g (2.96% by the total mass of the reagents) of anhydrous tetrahydrofuran and 150 g of anhydrous benzene. Through the bubbling means dry hydrogen chloride is passed at the rate of 1 l/hr for 5 hours, whereafter the reaction mixture is maintained in a refrigerator for 18 hours at the temperature of +6° C. and then treated under vigorous stirring at the temperature of −2° C. with 100 ml of ice-cold water for 2 hours. After stratification of the reaction mass into two layers, the oily phase is separated from the aqueous layer; the oily phase contains the desired product, residual amounts of the starting reagents and hydrogen chloride. It is washed with a 5% aqueous solution of sodium bicarbonate (150–200 ml) and water (100 ml) until no chlorine ion is detected and dried over anhydrous sodium sulphate.

The solvent is distilled-off in vacuum of 20–30 mm Hg and 0.01 mm Hg and the residue is recrystallized from a mixture of diethyl ether with petroleum ether. The product has the following physico-chemical characteristics.

Elemental analysis: Found, % by mass: C 57.80 H 6.01 N 5.03 Cl 13.20. ($C_{26}H_{32}N_2Cl_2O_6$). Calculated, % by mass: C 57.88 H 5.94 N 5.19 Cl 13.17.

Gas number (cm$^3$/g): Found: 41.5. Calculated: 41.5.

Cryoscopic molecular mass (in dioxane): Calculated: 539. Found: 530.

Ester number (mg KOH/g): Found: 205. Calculated: 208.

In the IR-spectrum (CCl$_4$, thin layer) there is observed an absorption band with the frequency $\nu=1.745$ cm$^{-1}$ corresponding to the bond C=O, the frequency $\nu-1.680$ cm$^{-1}$ corresponding to the aromatic ring, $\nu=820$ cm$^{-1}$ corresponding to the bond C—Cl, $\nu=1.040$ cm$^{-1}$ (ROAr), $\nu=1.568$ cm$^{-1}$ correspondingto the bond —N=N—.

In the UV-spectrum (ethyl, benzene) there is observed an absorption band maximum at the wavelength $\lambda_{max}=365$ nm corresponding to the bond —N=N— and coefficient $\epsilon=26$; according to these data the product corresponds to the formula: α,ω-bis-[(ω)-p-(chloromethyl)phenyl]oxyethylene ester of α,α'-azo-bis-isobutyric acid.

The resulting desired product is useful as an initiator of a radical polymerization of styrene and as a starting component in the manufacture of reactive polymers.

Described hereinbelow is the use of α,ω-bis-/ω-p-(chloromethyl)phenyl/oxyethylene ester of α,α'-azo-bis-isobutyric acid in polymerization of styrene which is effected in the following manner.

100 ml of styrene containing $5.10^{-4}$ mol of α,ω-bis-/ω-(p-chloromethyl)phenyl oxyethylene ester of α,α'-azo-bis-isobutyric acid are heated to the temperature of 85° C. under anaerobic conditions and maintained at this temperature for a period of several hours. The polymerization rate is controlled by increasing density of the reaction mass thus demonstrating the formation of polystyrene.

The rate of polymerization under these conditions at the degree of conversion of 5% is $9.7 \times 10^{-3}$ mol/l, at the conversion of 10%—$9.2 \times 10^{-3}$ mol/l. The rate of polymerization of styrene in the absence of the initiator at the conversion values of 5 and 10% is equal to $0.92 \times 10^{-3}$ mol/l.

The manufacture of reactive polydivinyl with azo group in the polymeric chain is effected in the following manner.

To a solution of 100 ml of α,ω-bis(lithium) oligodivinyl with the molecular mass of 1,000 in 450 ml of toluene at the temperature of 25° C. there is added a solution of a stoichiometric amount of α,ω-bis-/ω-p(chloromethyl)phenyl/oxyethylene ester of α,α'-azo-bis-isobutyric acid in toluene (150 ml) and the mixture is stirred for two hours.

The formation of reactive polydivinyl is detected by increasing intrinsic viscosity of polydivinyl (at the temperature of 25° C. in toluene) from 1.73 to 3.22 dl/g and by the formation of lithium chloride precipitate.

EXAMPLE 15

The synthesis is carried out as described in the foregoing Example 14, except that as the derivative of the monohydric saturated alkyl alcohol use is made of n-chloromethylphenol and as the solvent—n-pentane, while as the water-soluble ether use is made of dioxane.

The thus-prepared compound has the following physico-chemical characteristics:

Elemental analysis: Found, % by mass: C 58,23; H 5.40; N 6.11; Cl 15.91. $C_{22}H_{24}Cl_2N_2O_4$. Calculated, % by mass: C 58.84; H 5.32; N 6.21; Cl 15.74.

Gas number (cm$^3$/g): Found: 49.2. Calculated: 49.6.

Cryoscopic molecular mass (in benzene): Found: 449. Calculated: 451.

Ester number (mg KOH/g): Found: 247. Calculated: 249.

In the IR-spectrum (CCl$_4$, thin layer) there is observed an absorption band with the frequency $\nu=1,765$ cm$^{-1}$ corresponding to the bond C=O, $\nu=1,680$ cm$^{-1}$ corresponding to the aromatic ring, $\nu=820$ cm$^{-1}$ corresponding to the bond C—Cl, $\nu=1,568$ cm$^{-1}$ corresponding to the bond —N=N—.

In the UV-spectrum (ethylbenzene) there is observed an absorption band maximum at the wavelength $\lambda_{max}=365$ nm corresponding to the bond —N=N— and coefficient $\epsilon=26$; according to these data the product has the formula: α,ω-bis-/n-(chloromethyl)-phenyl/ester of α,α'-azo-bis-isobutyric acid.

The desired product yield is 65% of the theoretical.

EXAMPLE 16

The synthesis is conducted in a manner similar to that described in Example 14, except that as the derivative of an alkyl monohydric saturated alcohol use is made of ω-[n-(chloromethyl)phenyl]ethanol and as the solvent use is made of diethyl ether, while as the water-soluble ether use is made of diethylene glycol dimethylate.

The thus-prepared compound has the following characteristics:

Elemental analysis: Found, % by mass: C 61.25; H 6.70; N 5.40; Cl 14.30. $C_{26}H_{32}N_2O_4Cl_2$. Calculated, % by mass: C 61.54; H 6.31; N 5.52; Cl 14.00.

Gas number (cm$^3$/g): Found: 43.8. Calculated: 44.0.

Cryoscopic molecular mass (dioxane): Found: 502. Calculated: 507.

Ester number (mg KOH/g): Found 225. Calculated 221.

In the IR-spectrum (CCl$_4$, thin layer) an absorption band is observed at the frequency of 1,740 cm$^{-1}$ corresponding to the bond C=O, $\nu=1,680$ cm$^{-1}$ corresponding to the aromatic ring; $\nu=820$ cm$^{-1}$ corresponding to the bond C—Cl, $\nu=1.568$ cm$^{-1}$ corresponding to the bond —N=N—.

In the UV-spectrum (ethylbenzene) there is observed an absorption band maximum at the wavelength $\nu_{max}=365$ nm corresponding to the bond —N=N— and coefficient $\epsilon=26$; these data make it possible to attribute, to the product, the formula: α,ω-bis-/ω-[p-(chloromethyl)phenyl]ethyl/ester of α,α'-azo-bis-isobutyric acid.

The resulting compound is useful as an initiator of a radical polymerization of divinyl which is effected in the following manner.

Divinyl and α,ω-bis-/ω-/n-chloromethyl)phenyl/ethyl/ester of α,α'-azo-bis-isobutyric acid are dissolved in thoroughly dried dioxane. The solution is exempted of oxygen dissolved therein and then thermostatted at the temperature of 65° C.

The experiment conditions and the final product characteristics are shown in the following Table.

| No. | Monomer concentration, mol/l | Initiator concentration, mol/l | Time, hours | Yield, % by mass | Molecular mass |
|---|---|---|---|---|---|
| 1 | 5 | 3 | 70 | 30 | 2,500 |
| 2 | 10 | 3 | 70 | 30 | 3,900 |

The product is recovered by the removal of the monomer residual amounts and the initiator by outgassing and reprecipitation. The presence of chlorine in the oligomer is checked by the qualitative determination of chlorine by the Folghardt method.

The resulting oligomers of divinyl with p-(chloromethyl)-phenyl groups are employed for the production of reactive polymers. To this end, the oligodivinyl in the amount of 100 m is dissolved in 450 ml of toluene. The solution is added with the equimolar amount of N,N′-(dimethyl)-hexamethylene diamine at the temperature of 20° C. One hour after, the solution viscosity is increased from 1.7 to 4.5 dl/g. For the purpose of comparison, the oligodivinyl with terminal groups

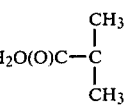

under the same conditions does not substantially enter into the reaction with N,N′-(dimethyl)-hexamethylene diamine, since the viscosity of the resulting solution is varied from 1.6 to 2.0 dl/g.

EXAMPLE 17

The synthesis is carried out as described in Example 14, except that as the hydroxyl-containing compound use is made of ω-/p-(chloromethyl)phenyl/propanol and as the solvent—methylene chloride.

The resulting product has the following physico-chemical characteristics:

Elemental composition: Found, % by mass: C 62.0; H 6.80; N 4.95; Cl 13.50. $C_{28}H_{36}N_2O_4Cl$. Calculated, % by mass: C 62.80; H 6.73; N 5.23; Cl 13.27.

Gas number ($cm^3/g$): Found: 45.8. Calculated: 46.0.

Molecular mass (cryoscopic, dioxane): Found: 530. Calculated: 532.

Ester number (mg KOH/g), Found: 208. Calculated: 210.

In the IR-spectrum ($CCl_4$, thin layer) there is observed an absorption band at the frequency $\nu=1.740$ $cm^{-1}$ corresponding to the bond C=O, $\nu=1.680$ $cm^{-1}$ corresponding to the aromatic ring, $\nu=820$ $cm^{-1}$ corresponding to the bond C—Cl, $\nu=1,568$ $cm^{-1}$ corresponding to the bond —N=N—.

In the UV-spectrum (ethylbenzene) there is observed an absorption band maximum at the wavelength $\lambda_{max}=365$ nm corresponding to the bond —N=N— and coefficient $\epsilon=26$; according to these data, the product has the formula: α,ω-bis-/ω-[(p-chloromethyl)-phenyl]propyl ester of α,α′-azo-bis-isobutyric acid.

The desired product yield is 89% of the theoretical.

EXAMPLE 18

The synthesis is conducted as in Example 14 hereinbefore, except that as the hydroxyl-containing compound use is made of ω-/p-(chloromethyl)benzoate/ethanol.

The resulting compound has the following physico-chemical characteristics:

Elemental analysis: Found, % by mass: C 56.50; H 5.50; N 4.60; Cl 12.10. $C_{28}H_{32}Cl_2N_2O_8$. Calculated, % by mass: C 56.47; H 5.38; N 4.71; Cl 11.93.

Gas number ($cm^3/g$): found: 37.8. calculated: 37.6.

Cryoscopic molecular mass (dioxane): Found: 590. Calculated: 595.

Ester number (mg KOH/g): Found: 372. Calculated: 376.

In the IR-spectrum ($CCl_4$, thin layer) there is observed an absorption band at the frequency $\nu=1.740$ $cm^{-1}$ corresponding to the bond C=O; $\nu=1.680$ $cm^{-1}$ corresponding to the aromatic ring, $\nu=820$ $cm^{-1}$ corresponding to the bond C—Cl, $\nu=1,568$ $cm^{-1}$ corresponding to the bond —N=N—.

In the UV-spectrum (ethylbenzene) there is observed an absorption band maximum at the wavelength $\lambda_{max}=365$ nm corresponding to the bond —N=N— and coefficient $\epsilon=26$; according to these data the resulting product corresponds to the formula: α,ω-bis-/ω-/p-(chloromethyl)benzoate/ethyl ester of α,α′-azo-bis-isobutyric acid.

What is claimed is:

1. α,α′-Azo-bis-isobutyric acid α,ω-bis-alkyl ester derivatives of the formula:

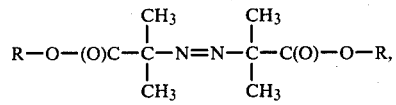

wherein R:

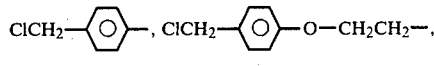

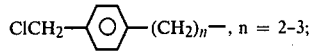

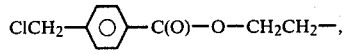

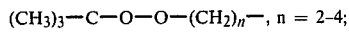

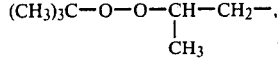

2. A method for preparing α,α′-azo-bis-isobutyric acid α,ω-bis-alkyl ester derivatives of the formula:

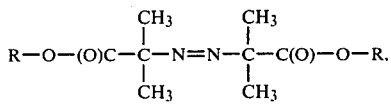

wherein R:

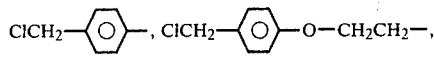

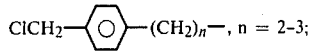

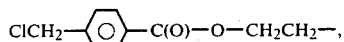

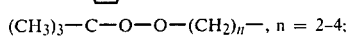

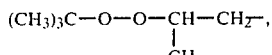

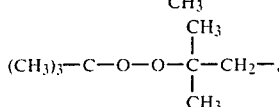

comprising reacting α,α'-azo-bis-isobutyric acid dinitrile and a saturated alkyl monohydric derivative of the formula ROH, wherein R is:

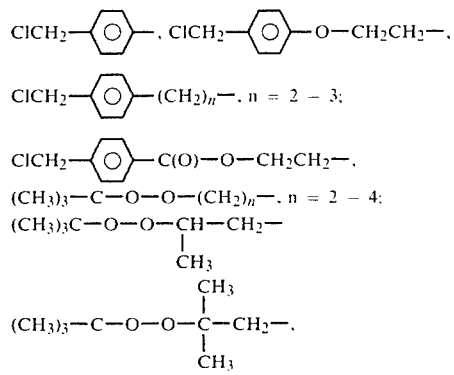

with gaseous hydrogen chloride in an organic solvent medium in the presence of 0.5 to 5% by mass of a water-soluble ether at a temperature within the range of from −5° to +6° C., followed by treating the resulting reaction mixture with water at a temperature of from 0° to −5° C. and isolation of the desired product.

3. A method according to claim 2, wherein the ester derivative is α,ω-bis(tert.butylperoxyethyl) ester of α,α'-azo-bis-isobutyric acid.

4. A method according to claim 2, wherein the ester derivative is α,ω-bis(tert.butylperoxybutyl) ester of α,α'-azo-bis-isobutyric acid.

5. A method according to claim 2, wherein the ester derivative is α,ω-bis-oxyethylene ester of α,α'-azo-bis-isobutyric acid.

6. A method according to claim 2, wherein the ester derivative is α,ω-bis-/ω-ethyl/ester of α,α'-azo-bis isobutyric acid.

7. A method according to claim 2, wherein the ester derivative is α,ω-bis-ω-/p-(chloromethyl)benzoate/ethyl ester of α,α'-azo-bis-isobutyric acid.

* * * * *